United States Patent
Akahata et al.

(10) Patent No.: US 10,166,281 B2
(45) Date of Patent: Jan. 1, 2019

(54) METHOD AND COMPOSITION FOR MODULATING IMMUNE RESPONSE

(71) Applicant: VLP Therapeutics, LLC, Wilmington, DE (US)

(72) Inventors: Wataru Akahata, Kensington, MD (US); Ryuji Ueno, Easton, MD (US)

(73) Assignee: VLP Therapeutics, LLC, Wilmington, DE (US)

( * ) Notice: Subject to any disclaimer, the term of this patent is extended or adjusted under 35 U.S.C. 154(b) by 15 days.

(21) Appl. No.: 15/255,294

(22) Filed: Sep. 2, 2016

(65) Prior Publication Data

US 2017/0065703 A1 Mar. 9, 2017

Related U.S. Application Data

(60) Provisional application No. 62/214,477, filed on Sep. 4, 2015.

(51) Int. Cl.
*A61K 39/12* (2006.01)
*A61K 39/00* (2006.01)

(52) U.S. Cl.
CPC ...... *A61K 39/12* (2013.01); *A61K 2039/5258* (2013.01); *A61K 2039/585* (2013.01); *C12N 2770/36123* (2013.01); *C12N 2770/36133* (2013.01); *C12N 2770/36134* (2013.01)

(58) Field of Classification Search
CPC ........... C12N 2740/10023; C12N 2770/36111; C07K 14/1808; C07K 16/1081; Y02A 50/382
See application file for complete search history.

(56) References Cited

U.S. PATENT DOCUMENTS

| | | | | |
|---|---|---|---|---|
| 9,249,191 | B2 * | 2/2016 | Ueno | C07K 14/005 |
| 9,353,353 | B2 * | 5/2016 | Nabel | A61K 39/12 |
| 9,487,563 | B2 * | 11/2016 | Nabel | A61K 39/12 |
| 9,512,190 | B2 * | 12/2016 | Ueno | A61K 38/162 |
| 9,637,532 | B2 * | 5/2017 | Akahata | C07K 14/70503 |
| 2012/0003266 | A1 | 1/2012 | Nable et al. | |
| 2014/0170186 | A1 | 6/2014 | Nabel et al. | |
| 2016/0040134 | A1 | 2/2016 | Akahata et al. | |

FOREIGN PATENT DOCUMENTS

WO WO 2012/106356 A2 * 8/2012

OTHER PUBLICATIONS

Akahata et al. Nat, Med. Mar. 2010; 16 (3), pp. 334-338.*
Metz et al. .PLoS ONE, 2011, vol. 6, Issue 10, pp. 1-10.*
Antonio Roldao et al., "Virus-like particles in vaccine development", Expert Rev. Vaccines 9(10), 2010, pp. 1149-1176.
Wataru Akahata et al., "A VLP vaccine for epidemic Chikungunya virus protects nonhuman primates against infection", Nat Med., Mar. 2010, 16(3), pp. 334-338 (12 pgs. total).

\* cited by examiner

*Primary Examiner* — Bao Q Li
(74) *Attorney, Agent, or Firm* — Sughrue Mion, PLLC

(57) ABSTRACT

Provided is a method for modulating an immune response which is not derived from alphavirus infection comprising administering to a subject in need thereof an effective amount of a composition comprising an alphavirus virus like particle.

7 Claims, 1 Drawing Sheet
Specification includes a Sequence Listing.

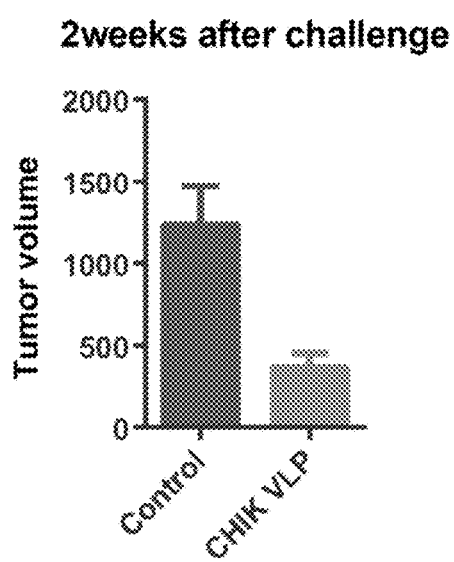

METHOD AND COMPOSITION FOR MODULATING IMMUNE RESPONSE

CROSS REFERENCE TO RELATED APPLICATION

This application claims benefit of U.S. Provisional Application No. 62/214,477 filed Sep. 4, 2015, the contents of which are incorporated by reference.

TECHNICAL FIELD

The present application relates to a method and composition for modulating an immune response with an alphavirus virus like particle.

BACKGROUND ART

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: GlaxoSmithKline's Engerix® (hepatitis B virus) and Cervarix® (human papillomavirus), and Merck and Co., Inc.'s Recombivax HB® (hepatitis B virus) and Gardasil® (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination.

Up to now, VLP-based vaccines have been produced for more than 30 different viruses that infect human and other animals. The examples include AAV (Adeno-associated virus), H5N3 (Avian influenza), BFDV (Budgerigar fledgling disease virus), BTV (Bluetongue virus), Ebola, Enterovirus 71, GHPV (Goose hemorrhagic polyoma virus), HBV (Hepatitis B virus), HCV (Hepatitis C virus), HDV (Hepatitis δ virus), HEV (Hepatitis E virus), HIV, HPV (Human papillomavirus), IBDV (Infectious bursal disease virus), Influenza A, Influenza A H1N1, Influenza A H3N2, JC polymavirus, Margurg, MS2, IPCV (Indian peanut clump virus), NDV (Newcastle disease virus), No (Norovirus) Nv (Norwalk virus), PhMV (Physalis mottle virus), Polymavirus, PPV (Porcine parvovirus), RHDV (Rabbit hemorrhagic disease virus), Rotavirus, SARS, SIV (Simian immunodeficiency virus), SV40 (Simian virus 40), SVDV (Swine vesicular disease virus) and so on. (Expert Rev. Vaccines 9(10), 1149-1176, 2010).

Chikungunya virus (CHIKV) is a member of alphavirus and has infected millions of people in Africa, Europe and Asia since this alphavirus reemerged from Kenya in 2004. The severity of the disease and the spread of this epidemic virus present a serious public health threat in the absence of vaccines or antiviral therapies. It is reported that a VLP vaccine for epidemic Chikungunya virus protects non-human primates against infection (Nat Med. 2010 March; 16(3): 334-338). US patent publication No. 2012/0003266 discloses a virus-like particle (VLP) comprising one or more Chikungunya viral structural proteins which is useful for formulating a vaccine or antigenic composition for Chikungunya that induces immunity to an infection or at least one symptom thereof. US patent publication No. 2014/170186 discloses modified alphavirus or flavivirus virus-like particles (VLPs) and methods for enhancing production of modified VLPs for use in the prevention or treatment of alphavirus and flavivirus-mediated diseases. (these cited references are herein incorporated by reference).

SUMMARY OF INVENTION

The present application relates to a method and composition for modulating an immune response which is not derived from alphavirus infection comprising administering to a subject in need thereof an effective amount of a composition comprising an alphavirus virus like particle.

The present application relates to a method and composition for the treatment or prophylaxis of an immune-related disease which is not derived from alphavirus infection comprising administering to a subject in need thereof an effective amount of a composition comprising an alphavirus virus like particle.

The present application relates to an immunostimulant comprising an effective amount of a composition comprising an alphavirus virus like particle.

BRIEF DESCRIPTION OF DRAWINGS

FIG. 1 shows that tumor size was shrunk by CHIK VLP.

DESCRIPTION OF EMBODIMENTS (1) Alphavirus Virus Like Particle

Alphavirus virus like particle used in the present application is composed of one or more alphavirus viral structural proteins that spontaneously assemble into a particulate structure.

Alphavirus viral structural protein used in the present application may be an alphavirus envelope protein and/or a capsid protein and/or a fragment thereof and/or a complex of one or more envelope proteins and/or a capsid protein and/or a fragment thereof.

Examples of alphavirus include, but not limited to, Aura virus, Babanki virus, Barmah Forest virus (BFV), Bebaru virus, Cabassou virus, Chikungunya virus (CHIKV), Eastern equine encephalitis virus (EEEV), Eilat virus, Everglades virus, Fort Morgan virus, Getah virus, Highlands J virus, Kyzylagach virus, Madariaga virus, Mayaro virus, Me In virus, Middelburg virus, Mosso das Pedras virus, Mucambo virus, Ndumu virus, Ockelbo virus, O'nyong-nyong virus, Pixuna virus, Rio Negro virus, Ross virus (RRV), Salmon pancreas disease virus, Semliki Forest virus, Sindbis virus, Southern elephant seal virus, Tonate virus, Trocara virus, Una virus, Venezuelan equine encephalitis virus (VEEV), Western equine encephalitis virus (WEEV) and Whataroa virus.

The particle provided by the present application may be a virus like particle derived from Chikungunya virus or Venezuelan equine encephalitis virus. Chikungunya virus may be Chikungunya virus 37997 strain or strain LR2006 OPY-1. Venezuelan equine encephalitis virus may be Venezuelan equine encephalitis virus TC-83 strain. A viral structural protein used in the present application may be a naturally occurring viral structural protein or a modified protein thereof. The modified protein may be a fragment of the naturally occurring viral structural protein. In one embodiment, the modified protein has at least 70%, 75%, 80%, 85%, 90%, 95% or 98% amino acid sequence identity to a naturally occurring viral capsid and/or envelope protein. In one embodiment, the modified protein is a mutant where at most 10% of the amino acids are deleted, substituted, and/or added based on a naturally occurring viral capsid and/or envelope protein. For example, K64A or K64N mutation may be introduced into a capsid of Venezuelan equine encephalitis viral structural protein used in the present application.

The viral structural protein can be truncated and replaced by short linkers. In some embodiments, a viral structural protein includes one or more peptide linkers. Typically, a linker consists of from 2 to 25 amino acids (e.g. 2, 3, 4, 5 or 6 amino acids). Usually, it is from 2 to 15 amino acids in length, although in certain circumstances, it can be only one, such as a single glycine residue.

The viral structural protein may consist of or comprise a capsid, E3, E2 and E1 proteins. E3 and E2 proteins maybe expressed together so that E2 and E3 can form one protein.

Examples of the viral structural protein include, but are not limited to, Capsid-E3-E2-E1 of Chikungunya virus 37997 strain, Capsid-E3-E2-E1 of Chikungunya virus LR2006 OPY-1 strain, and Capsid-E3-E2-E1 of Venezuelan equine encephalitis virus TC-83 strain.

An exemplary Chikungunya viral structural protein sequence is provided at Genbank Accession No. ABX40006.1 (LR2006 OPY-1 strain, SEQ ID NO: 1).

Another exemplary Chikungunya viral structural protein sequence is provided at Genbank Accession No. ABX40011.1 (37997 strain, SEQ ID NO: 2).

An exemplary Venezuelan equine encephalitis viral structural protein is provided at Genbank Accession No. L01443.1 (http://www.ncbi.nlm.nih.gov/nuccore/L01443.1) (TC-83 strain, SEQ ID NO:12).

Under physiological conditions, E3 can be dissociated from E2 after furin cleavage. In another aspect, the present application provides a virus like particle comprising a modified envelope protein E3. In this aspect, the envelope protein E3 may be modified to comprise an alternation/mutation to the amino acid sequence at the furin site (Arg-X-X-Arg).

The viral structural protein of alpha virus consists of Capsid, E1, E2, 6K and E3. 6K is naturally cleaved during the process of assemble and removed from the VLPs. The mature VLPs consist of capsid, E1 and E2. In the present specification and claims, "viral structural protein" refers not only those having 6K but also after 6K is removed.

Examples of 6K sequences of the CHIKV used in the present invention are as follows:

```
CHIKV OPY-1 Strain, 6K: 749-809 aa of
SEQ ID NO: 1
                                        (SEQ ID NO: 3)
atyqeaaiylwneqqplfwlqaliplaalivlcnclrllpcccktlafla vmsvgahtvsa CHIKV 37997 strain, 6K: 749-809 aa of
SEQ ID NO: 2
                                        (SEQ ID NO: 4)
atyyeaaaylwneqqplfwlqaliplaalivlcnclkllpcccktlafla vmsigahtvsa
```

```
VEEV TC-83strain, 6K: 758-813 aa of
SEQ ID NO: 12
                                        (SEQ ID NO: 13)
ettwesldhlwnnnqqmfwiqlliplaalivvtrllrcvccvvpflvmag aagaga
```

The fusion protein may be expressed using a conventional technique in the art. A variety of expression systems can be used for the expression of the fusion protein. For example, the fusion protein can be expressed in 293F cells, Sf9 cells, *E. coli*, insect cell or Baculovirus.

A protein derived from alphavirus may be a naturally occurring viral protein or modified protein thereof.

In one embodiment, the present application provides a virus like particle comprising or consisting of:
one or more capsid of Chikungunya virus (CHIKV) or Venezuelan equine encephalitis virus (VEEV);
one or more E1 of Chikungunya virus (CHIKV) or Venezuelan equine encephalitis virus (VEEV);
one or more E2 of Chikungunya virus (CHIKV) or Venezuelan equine encephalitis virus (VEEV); or
one or more E3 of Chikungunya virus (CHIKV) or Venezuelan equine encephalitis virus (VEEV), wherein each of E2 is bound to each of E3. For example, present application also provides a virus like particle comprising or consisting of:
240 capsids of Chikungunya virus (CHIKV) or Venezuelan equine encephalitis virus (VEEV);
240 E1s of Chikungunya virus (CHIKV) or Venezuelan equine encephalitis virus (VEEV);
240 E2s of Chikungunya virus (CHIKV) or Venezuelan equine encephalitis virus (VEEV); or
240s E3s of Chikungunya virus (CHIKV) or Venezuelan equine encephalitis virus (VEEV), wherein each of E2 is bound to eachof E3.

Further, regarding these embodiments, modified capsid of Chikungunya virus (CHIKV) or Venezuelan equine encephalitis virus (VEEV), modified E1 of Chikungunya virus (CHIKV) or Venezuelan equine encephalitis virus (VEEV) and/or modified complex of E2 and E3 of Chikungunya virus (CHIKV) or Venezuelan equine encephalitis virus (VEEV) maybe used for the virus like particle. For example, the modified capsid of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 5, SEQ ID NO: 6 or SEQ ID NO:14; the modified E1 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 7, SEQ ID NO: 8 or SEQ ID NO: 15; and/or the modified complex of E2 and E3 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID No:9, SEQ ID NO: 10 or SEQ ID NO: 16. Also, the modified capsid, E1 and/or a complex of E2 and E3 may be a mutant where at most 10% of the amino acids are deleted, substituted, and/or added based on the capsid consisting of an amino acid sequence represented by SEQ ID NO: 5, SEQ ID NO: 6 or SEQ ID NO:14; E1 consisting of an amino acid sequence represented by SEQ ID NO: 7, SEQ ID NO: 8 or SEQ ID NO:15; and/or a complex of E2 and E3 consisting of consisting of an amino acid sequence represented by SEQ ID NO: 9, SEQ ID NO: 10 or SEQ ID NO: 16.

Virus like particle may be prepared by introducing an expression vector comprising a DNA molecule having a nucleotide sequence encoding the virus like particle into a cell (e.g. 293F cell), culturing the cell and recovering the virus like particle from the conditioned medium using ultracentrifugal method.

The VLPs described as above may be prepared by stable cell line. The stable cell line can be prepared by using the above-described vectors and according to conventional procedures. For example, the following procedures may be employed to generate a stable cell line:

1. Transfect cells such as 293F cells are transfected with a VLP expression plasmid containing selection marker such as hygromycin B.
2. Incubate the transfected cells for one day
3. Culture the transfected cells in a selection medium containing such as Hygromycin at 150-200 ug/ml for 1-2 weeks.
4. Choose the cells that can grow and be split at least once in the selection medium.
5. Isolate a single cell and confirm the expression of the VLP in the supernatants by western blotting.

In one embodiment, the virus like particle may be prepared according to the method described in US patent publication Nos. 2012-0003266, 2014-170186 or 2016-0040134.

(2) Method and Composition

The present application provides a method and composition for modulating an immune response which is not derived from alphavirus infection comprising administering to a subject in need thereof an effective amount of a composition comprising an alphavirus virus like particle.

The present application provides a method and composition for the treatment or prophylaxis of an immune-related disease which is not derived from alphavirus infection comprising administering to a subject in need thereof an effective amount of a composition comprising an alphavirus virus like particle.

The present application also provides an immunostimulant comprising an effective amount of a composition comprising an alphavirus virus like particle.

In one embodiment, the present application provides a pharmaceutical composition or a kit comprising a composition comprising an alphavirus virus like particle; and a pharmaceutically acceptable carrier. The amount of the alphavirus virus like particle in the composition may be 0.00001-1 w/w % of the pharmaceutical composition.

Dosage amount of the CHIK VLP or VEEV VLP provided by the present application may be 1-500 μg/day.

The pharmaceutical composition may further comprise an adjuvant. Examples of adjuvants include, but are not limited to, Ribi solution (Sigma Adjuvant system, Sigma-Aldrich). The pharmaceutical composition provided by the present application may contain a buffering agent such as dibasic sodium phosphate hydrate, sodium dihydrogen phosphate and sodium chloride; and a preserving agent such as thimerosal. In one embodiment, the pharmaceutical composition is an aqueous solution containing 0.001-1 w/w % of a particle, 1-10 w/w % of buffering agent, 0.01-1 w/w % of adjuvant and 0.00001-0.001 w/w % of preserving agent.

A skilled person can prepare the pharmaceutical composition using a conventional technique. For example, a particle comprising a viral structural protein is mixed with a buffer solution having physiological pH (e.g. pH 5-9, such as pH7) to prepare the pharmaceutical composition.

In one embodiment, the pharmaceutical composition is a vaccine or an immunostimulant comprising a particle comprising an alphavirus viral structural protein.

In one embodiment, the pharmaceutical composition is a DNA vaccine comprising a nucleic acid molecule comprising a nucleotide sequence for expressing a particle which comprises a viral structural protein. In one embodiment, the DNA vaccine provided by the present application comprises CpG containing oligonucleotide. One skilled in the art may prepare the nucleic acid molecule of the present application described above based on an exemplary nucleotide sequences of alphavirus viral structural protein that encode capsid and/or envelope represented by SEQ ID No:11 or SEQ ID NO: 17. A nucleic acid molecule consisting of a nucleotide sequence which has a sequence identity of 70%, 80%, 90%, 95% or 98% or more with the nucleotide sequence represented by SEQ ID No:11 or SEQ ID NO: 17 is also provided.

The pharmaceutical composition of the present application can be administered one or more times. When the pharmaceutical composition provided in the third aspect of the present application is administered more than one time, different particles provided in the first aspect of the present application may be used for each of the administration.

A skilled person can determine timing of immunization using the composition or vaccine provided by the present application. For example, a 2nd immunization is performed 1, 2, 3, 4, 5, 6, 7, 8, 9 or 10 weeks after a 1st immunization.

For example, the virus like particle comprising or consisting of:

one or more (e.g. 240) capsid of Chikungunya virus (CHIKV) or Venezuelan equine encephalitis virus (VEEV);
one or more (e.g. 240) E1 of Chikungunya virus (CHIKV) or Venezuelan equine encephalitis virus (VEEV);
one or more (e.g. 240) E2 of Chikungunya virus (CHIKV) or Venezuelan equine encephalitis virus (VEEV); and
one or more (e.g. 240) E3 of Chikungunya virus (CHIKV) or Venezuelan equine encephalitis virus (VEEV), wherein each of E2 is bound to each of E3.

The pharmaceutical composition may be administered to a mammal (e.g. human) intramuscularly (i.m.), intracutaneously (i.c.), subcutaneously (s.c.), intradermally (i.d.) or intraperitoneally (i.p.).

The composition of the present application is useful for immunotherapy to any immune related disease as long as improving immune function.

Examples of the immune related diseases to be treated may include leukopenia, immunodeficiency, cancer or infectious disease. autoimmune disease.

The term "treating" or "treatment" used herein includes prophylactic and therapeutic treatment, and any means of control such as prevention, care, relief of the condition, attenuation of the condition, arrest of progression, etc.

Examples of the cancer which may be treated include, but are not limited to, melanoma, renal cancer, prostate cancer, breast cancer, colon cancer and non-small cell lung cancer. Other examples of the cancer include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof.

Examples of infectious disease which may be treated include, but are not limited to, HIV, Influenza, Herpes, Giardia, Malaria, Leishmania, the pathogenic infection by the virus Hepatitis (A, B and C), herpes virus (e.g., VZV, HSV-I, HAV-6, HSV-II, and CMV, Epstein Barr virus), alphavirus (except for Chikungunya), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia, rickettsial bacteria, mycobacteria, staphylococci, streptococci, pneumonococci, meningococci* and *conococci, klebsiella, proteus, serratia, pseudomonas, legionella, diphtheria, salmonella, bacilli, cholera, tetanus, botulism, anthrax, plague, leptospirosis*, and Lymes disease bacteria, pathogenic infection by the fungi *Candida* (*albicans, krusei, glabrata, tropicalis*, etc.), *Cryptococcus neoformans, Aspergillus* (*fumigatus, niger*, etc.), *Genus Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Examples of autoimmune disease which may be treated include, but are not limited to, Addison's disease, Celiac disease, Crohn's disease, dermatomyositis, Graves' disease, Hashimoto's thyroiditis, multiple sclerosis, myasthenia gravis, psoriasis, pernicious anemia, reactive arthritis, rheumatoid arthritis, Sjogren syndrome, systemic lupus erythematosus, type I diabetes and ulcerative colitis.

The present application also provides a personalized therapy. In one embodiment, peripheral blood mononuclear cells (PBMCs) from patient will be isolated, the PBMCs from the patient will be cultured with VLPs for in vitro expansion, then the stimulated PBMCs will be transferred back to the patient.

The present application will be described in detail with reference to the following examples, which, however, are not intended to limit the scope of the present application.

EXAMPLE 1

Immunomodulation of Chikungunya Virus Like Particle

A Chikungunya virus like particle (CHIK VLP) derived from CHIKV 37997 strain (SEQ ID NO: 2) was used.

6-8 week-old male mice (8 per group) were injected with CHIK VLP (10 μg/mouse, i.m.) or PBS (control) on 0, 3 and 6 weeks. The mice were challenged with B16F10 cell lines ($1 \times 10^5$ cells)by s.q. at 8 weeks. Tumor sizes were measured 2 weeks after challenge and volume ($mm^3$) was calculated as: (length×(width)$^2$)/2.

The result is shown in FIG. 1. As seen in FIG. 1, tumor size was shrunk by CHIK VLP. The data indicates that CHIK VLP could enhance an immune response.

What is claimed is:

1. A method for modulating an immune response against a cancer, wherein said method comprises administering, to a subject with a cancer, an effective amount of a composition comprising an alphavirus virus like particle, wherein said alphavirus virus like particle does not contain a heterologous antigen.

2. The method of claim 1, wherein said modulating is the enhancement of an immune response against said cancer.

3. The method of claim 1, wherein the virus like particle comprises a viral structural protein of Chikungunya strain OPY-1, Chikungunya strain 37997 or Venezuelan equine encephalitis virus TC-83 strain.

4. The method of claim 1, wherein the alphavirus is Chikungunya virus.

5. The method of claim 2, wherein the alphavirus is Chikungunya virus.

6. The method of claim 3, wherein the alphavirus is Chikungunya virus.

7. The method of claim 3, wherein the viral structural protein is a viral structural protein of Chikungunya strain OPY-1 or Chikungunya strain 37997.

* * * * *

SEQUENCE LISTING

<160> NUMBER OF SEQ ID NOS: 17

<210> SEQ ID NO 1
<211> LENGTH: 1248
<212> TYPE: PRT
<213> ORGANISM: Chikungunya virus
<220> FEATURE:
<221> NAME/KEY: misc_feature
<222> LOCATION: (749)..(809)
<223> OTHER INFORMATION: 6K Protein

<400> SEQUENCE: 1

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Lys Pro Ala Gln Lys Lys
                85                  90                  95

```
Lys Lys Pro Gly Arg Arg Glu Arg Met Cys Met Lys Ile Glu Asn Asp
            100                 105                 110
Cys Ile Phe Glu Val Lys His Glu Gly Lys Val Thr Gly Tyr Ala Cys
            115                 120                 125
Leu Val Gly Asp Lys Val Met Lys Pro Ala His Val Lys Gly Thr Ile
            130                 135                 140
Asp Asn Ala Asp Leu Ala Lys Leu Ala Phe Lys Arg Ser Ser Lys Tyr
145                 150                 155                 160
Asp Leu Glu Cys Ala Gln Ile Pro Val His Met Lys Ser Asp Ala Ser
                165                 170                 175
Lys Phe Thr His Glu Lys Pro Glu Gly Tyr Tyr Asn Trp His His Gly
            180                 185                 190
Ala Val Gln Tyr Ser Gly Gly Arg Phe Thr Ile Pro Thr Gly Ala Gly
            195                 200                 205
Lys Pro Gly Asp Ser Gly Arg Pro Ile Phe Asp Asn Lys Gly Arg Val
            210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
                245                 250                 255
Gly Ala Glu Glu Trp Ser Leu Ala Ile Pro Val Met Cys Leu Leu Ala
            260                 265                 270
Asn Thr Thr Phe Pro Cys Ser Gln Pro Pro Cys Thr Pro Cys Cys Tyr
            275                 280                 285
Glu Lys Glu Pro Glu Glu Thr Leu Arg Met Leu Glu Asp Asn Val Met
            290                 295                 300
Arg Pro Gly Tyr Tyr Gln Leu Leu Gln Ala Ser Leu Thr Cys Ser Pro
305                 310                 315                 320
His Arg Gln Arg Arg Ser Thr Lys Asp Asn Phe Asn Val Tyr Lys Ala
                325                 330                 335
Thr Arg Pro Tyr Leu Ala His Cys Pro Asp Cys Gly Glu Gly His Ser
            340                 345                 350
Cys His Ser Pro Val Ala Leu Glu Arg Ile Arg Asn Glu Ala Thr Asp
            355                 360                 365
Gly Thr Leu Lys Ile Gln Val Ser Leu Gln Ile Gly Ile Lys Thr Asp
            370                 375                 380
Asp Ser His Asp Trp Thr Lys Leu Arg Tyr Met Asp Asn His Met Pro
385                 390                 395                 400
Ala Asp Ala Glu Arg Ala Gly Leu Phe Val Arg Thr Ser Ala Pro Cys
                405                 410                 415
Thr Ile Thr Gly Thr Met Gly His Phe Ile Leu Ala Arg Cys Pro Lys
            420                 425                 430
Gly Glu Thr Leu Thr Val Gly Phe Thr Asp Ser Arg Lys Ile Ser His
            435                 440                 445
Ser Cys Thr His Pro Phe His His Asp Pro Pro Val Ile Gly Arg Glu
            450                 455                 460
Lys Phe His Ser Arg Pro Gln His Gly Lys Glu Leu Pro Cys Ser Thr
465                 470                 475                 480
Tyr Val Gln Ser Thr Ala Ala Thr Thr Glu Glu Ile Glu Val His Met
                485                 490                 495
Pro Pro Asp Thr Pro Asp Arg Thr Leu Met Ser Gln Gln Ser Gly Asn
            500                 505                 510
```

```
Val Lys Ile Thr Val Asn Gly Gln Thr Val Arg Tyr Lys Cys Asn Cys
            515                 520                 525

Gly Gly Ser Asn Glu Gly Leu Thr Thr Asp Lys Val Ile Asn Asn
530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
    595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
                660                 665                 670

Ala His Gly His Pro His Glu Ile Ile Leu Tyr Tyr Glu Leu Tyr
            675                 680                 685

Pro Thr Met Thr Val Val Val Ser Val Ala Thr Phe Ile Leu Leu
            690                 695                 700

Ser Met Val Gly Met Ala Ala Gly Met Cys Met Cys Ala Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
                740                 745                 750

Glu Ala Ala Ile Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
```

```
                930             935             940
Leu Tyr Gln Gly Asn Asn Ile Thr Val Thr Ala Tyr Ala Asn Gly Asp
945                 950             955                 960

His Ala Val Thr Val Lys Asp Ala Lys Phe Ile Val Gly Pro Met Ser
            965                 970             975

Ser Ala Trp Thr Pro Phe Asp Asn Lys Ile Val Val Tyr Lys Gly Asp
                980             985                 990

Val Tyr Asn Met Asp Tyr Pro Pro Phe Gly Ala Gly Arg Pro Gly Gln
            995             1000            1005

Phe Gly Asp Ile Gln Ser Arg Thr Pro Glu Ser Lys Asp Val Tyr
    1010            1015            1020

Ala Asn Thr Gln Leu Val Leu Gln Arg Pro Ala Val Gly Thr Val
    1025            1030            1035

His Val Pro Tyr Ser Gln Ala Pro Ser Gly Phe Lys Tyr Trp Leu
    1040            1045            1050

Lys Glu Arg Gly Ala Ser Leu Gln His Thr Ala Pro Phe Gly Cys
    1055            1060            1065

Gln Ile Ala Thr Asn Pro Val Arg Ala Val Asn Cys Ala Val Gly
    1070            1075            1080

Asn Met Pro Ile Ser Ile Asp Ile Pro Glu Ala Ala Phe Thr Arg
    1085            1090            1095

Val Val Asp Ala Pro Ser Leu Thr Asp Met Ser Cys Glu Val Pro
    1100            1105            1110

Ala Cys Thr His Ser Ser Asp Phe Gly Gly Val Ala Ile Ile Lys
    1115            1120            1125

Tyr Ala Ala Ser Lys Lys Gly Lys Cys Ala Val His Ser Met Thr
    1130            1135            1140

Asn Ala Val Thr Ile Arg Glu Ala Glu Ile Glu Val Glu Gly Asn
    1145            1150            1155

Ser Gln Leu Gln Ile Ser Phe Ser Thr Ala Leu Ala Ser Ala Glu
    1160            1165            1170

Phe Arg Val Gln Val Cys Ser Thr Gln Val His Cys Ala Ala Glu
    1175            1180            1185

Cys His Pro Pro Lys Asp His Ile Val Asn Tyr Pro Ala Ser His
    1190            1195            1200

Thr Thr Leu Gly Val Gln Asp Ile Ser Ala Thr Ala Met Ser Trp
    1205            1210            1215

Val Gln Lys Ile Thr Gly Gly Val Gly Leu Val Val Ala Val Ala
    1220            1225            1230

Ala Leu Ile Leu Ile Val Val Leu Cys Val Ser Phe Ser Arg His
    1235            1240            1245

<210> SEQ ID NO 2
<211> LENGTH: 1248
<212> TYPE: PRT
<213> ORGANISM: Chikungunya virus
<220> FEATURE:
<221> NAME/KEY: misc_feature
<222> LOCATION: (749)..(809)
<223> OTHER INFORMATION: 6K Protein

<400> SEQUENCE: 2

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30
```

-continued

```
Arg Pro Gln Arg Gln Ala Gly Gln Leu Ala Gln Leu Ile Ser Ala Val
         35                  40                  45
Asn Lys Leu Thr Met Arg Ala Val Pro Gln Lys Pro Arg Arg Asn
 50                  55                  60
Arg Lys Asn Lys Lys Gln Arg Gln Lys Gln Ala Pro Gln Asn Asp
 65                  70                  75                  80
Pro Lys Gln Lys Gln Pro Pro Gln Lys Pro Ala Gln Lys Lys
                 85                  90                  95
Lys Lys Pro Gly Arg Arg Glu Arg Met Cys Met Lys Ile Glu Asn Asp
                100                 105                 110
Cys Ile Phe Glu Val Lys His Glu Gly Lys Val Met Gly Tyr Ala Cys
            115                 120                 125
Leu Val Gly Asp Lys Val Met Lys Pro Ala His Val Lys Gly Thr Ile
        130                 135                 140
Asp Asn Ala Asp Leu Ala Lys Leu Ala Phe Lys Arg Ser Ser Lys Tyr
145                 150                 155                 160
Asp Leu Glu Cys Ala Gln Ile Pro Val His Met Lys Ser Asp Ala Ser
                165                 170                 175
Lys Phe Thr His Glu Lys Pro Glu Gly Tyr Tyr Asn Trp His His Gly
            180                 185                 190
Ala Val Gln Tyr Ser Gly Gly Arg Phe Thr Ile Pro Thr Gly Ala Gly
        195                 200                 205
Lys Pro Gly Asp Ser Gly Arg Pro Ile Phe Asp Asn Lys Gly Arg Val
    210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
                245                 250                 255
Gly Ala Glu Glu Trp Ser Leu Ala Leu Pro Val Leu Cys Leu Leu Ala
            260                 265                 270
Asn Thr Thr Phe Pro Cys Ser Gln Pro Pro Cys Thr Pro Cys Cys Tyr
        275                 280                 285
Glu Lys Glu Pro Glu Ser Thr Leu Arg Met Leu Glu Asp Asn Val Met
    290                 295                 300
Arg Pro Gly Tyr Tyr Gln Leu Leu Lys Ala Ser Leu Thr Cys Ser Pro
305                 310                 315                 320
His Arg Gln Arg Arg Ser Thr Lys Asp Asn Phe Asn Val Tyr Lys Ala
                325                 330                 335
Thr Arg Pro Tyr Leu Ala His Cys Pro Asp Cys Gly Glu Gly His Ser
            340                 345                 350
Cys His Ser Pro Ile Ala Leu Glu Arg Ile Arg Asn Glu Ala Thr Asp
        355                 360                 365
Gly Thr Leu Lys Ile Gln Val Ser Leu Gln Ile Gly Ile Lys Thr Asp
    370                 375                 380
Asp Ser His Asp Trp Thr Lys Leu Arg Tyr Met Asp Ser His Thr Pro
385                 390                 395                 400
Ala Asp Ala Glu Arg Ala Gly Leu Leu Val Arg Thr Ser Ala Pro Cys
                405                 410                 415
Thr Ile Thr Gly Thr Met Gly His Phe Ile Leu Ala Arg Cys Pro Lys
            420                 425                 430
Gly Glu Thr Leu Thr Val Gly Phe Thr Asp Ser Arg Lys Ile Ser His
        435                 440                 445
```

```
Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Glu Leu Tyr
        675                 680                 685

Pro Thr Met Thr Val Val Ile Val Ser Val Ala Ser Phe Val Leu Leu
690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
```

-continued

```
                    865                 870                 875                 880
        Ser Leu Pro Asp Tyr Ser Cys Lys Val Phe Thr Gly Val Tyr Pro Phe
                            885                 890                 895

Met Trp Gly Gly Ala Tyr Cys Phe Cys Asp Ala Glu Asn Thr Gln Leu
                            900                 905                 910

Ser Glu Ala His Val Glu Lys Ser Glu Ser Cys Lys Thr Glu Phe Ala
                            915                 920                 925

Ser Ala Tyr Arg Ala His Thr Ala Ser Ala Ser Ala Lys Leu Arg Val
                            930                 935                 940

Leu Tyr Gln Gly Asn Asn Ile Thr Val Ala Ala Tyr Ala Asn Gly Asp
        945                 950                 955                 960

His Ala Val Thr Val Lys Asp Ala Lys Phe Val Val Gly Pro Met Ser
                            965                 970                 975

Ser Ala Trp Thr Pro Phe Asp Asn Lys Ile Val Val Tyr Lys Gly Asp
                            980                 985                 990

Val Tyr Asn Met Asp Tyr Pro Pro Phe Gly Ala Gly Arg Pro Gly Gln
                            995                1000                1005

Phe Gly Asp Ile Gln Ser Arg Thr Pro Glu Ser Lys Asp Val Tyr
        1010                1015                1020

Ala Asn Thr Gln Leu Val Leu Gln Arg Pro Ala Ala Gly Thr Val
        1025                1030                1035

His Val Pro Tyr Ser Gln Ala Pro Ser Gly Phe Lys Tyr Trp Leu
        1040                1045                1050

Lys Glu Arg Gly Ala Ser Leu Gln His Thr Ala Pro Phe Gly Cys
        1055                1060                1065

Gln Ile Ala Thr Asn Pro Val Arg Ala Val Asn Cys Ala Val Gly
        1070                1075                1080

Asn Ile Pro Ile Ser Ile Asp Ile Pro Asp Ala Ala Phe Thr Arg
        1085                1090                1095

Val Val Asp Ala Pro Ser Val Thr Asp Met Ser Cys Glu Val Pro
        1100                1105                1110

Ala Cys Thr His Ser Ser Asp Phe Gly Gly Val Ala Ile Ile Lys
        1115                1120                1125

Tyr Thr Ala Ser Lys Lys Gly Lys Cys Ala Val His Ser Met Thr
        1130                1135                1140

Asn Ala Val Thr Ile Arg Glu Ala Asp Val Glu Val Glu Gly Asn
        1145                1150                1155

Ser Gln Leu Gln Ile Ser Phe Ser Thr Ala Leu Ala Ser Ala Glu
        1160                1165                1170

Phe Arg Val Gln Val Cys Ser Thr Gln Val His Cys Ala Ala Ala
        1175                1180                1185

Cys His Pro Pro Lys Asp His Ile Val Asn Tyr Pro Ala Ser His
        1190                1195                1200

Thr Thr Leu Gly Val Gln Asp Ile Ser Thr Thr Ala Met Ser Trp
        1205                1210                1215

Val Gln Lys Ile Thr Gly Gly Val Gly Leu Ile Val Ala Val Ala
        1220                1225                1230

Ala Leu Ile Leu Ile Val Val Leu Cys Val Ser Phe Ser Arg His
        1235                1240                1245

<210> SEQ ID NO 3
<211> LENGTH: 61
<212> TYPE: PRT
<213> ORGANISM: Artificial Sequence
```

<220> FEATURE:
<223> OTHER INFORMATION: Synthetic CHIKV OPY-1 strain 6K sequence

<400> SEQUENCE: 3

```
Ala Thr Tyr Gln Glu Ala Ala Ile Tyr Leu Trp Asn Glu Gln Gln Pro
1               5                   10                  15

Leu Phe Trp Leu Gln Ala Leu Ile Pro Leu Ala Ala Leu Ile Val Leu
            20                  25                  30

Cys Asn Cys Leu Arg Leu Leu Pro Cys Cys Cys Lys Thr Leu Ala Phe
        35                  40                  45

Leu Ala Val Met Ser Val Gly Ala His Thr Val Ser Ala
    50                  55                  60
```

<210> SEQ ID NO 4
<211> LENGTH: 61
<212> TYPE: PRT
<213> ORGANISM: Artificial Sequence
<220> FEATURE:
<223> OTHER INFORMATION: Synthetic CHIKV 37997 strain 6K sequence

<400> SEQUENCE: 4

```
Ala Thr Tyr Tyr Glu Ala Ala Ala Tyr Leu Trp Asn Glu Gln Gln Pro
1               5                   10                  15

Leu Phe Trp Leu Gln Ala Leu Ile Pro Leu Ala Ala Leu Ile Val Leu
            20                  25                  30

Cys Asn Cys Leu Lys Leu Leu Pro Cys Cys Cys Lys Thr Leu Ala Phe
        35                  40                  45

Leu Ala Val Met Ser Ile Gly Ala His Thr Val Ser Ala
    50                  55                  60
```

<210> SEQ ID NO 5
<211> LENGTH: 261
<212> TYPE: PRT
<213> ORGANISM: Artificial Sequence
<220> FEATURE:
<223> OTHER INFORMATION: Synthetic CHIKV Capsid (37997 strain)

<400> SEQUENCE: 5

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160
```

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260

<210> SEQ ID NO 6
<211> LENGTH: 261
<212> TYPE: PRT
<213> ORGANISM: Artificial Sequence
<220> FEATURE:
<223> OTHER INFORMATION: Synthetic CHIKV Capsid (OPY-1 strain)

<400> SEQUENCE: 6

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
         260

<210> SEQ ID NO 7
<211> LENGTH: 439
<212> TYPE: PRT
<213> ORGANISM: Artificial Sequence
<220> FEATURE:
<223> OTHER INFORMATION: Synthetic CHIKV E1 (37997 strain)

<400> SEQUENCE: 7

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Ala Ala Tyr Ala Asn Gly Asp His Ala Val Thr Val Lys Asp Ala Lys
145                 150                 155                 160

Phe Val Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Ile Pro Ile Ser Ile Asp Ile Pro Asp Ala Ala Phe Thr
        275                 280                 285

Arg Val Val Asp Ala Pro Ser Val Thr Asp Met Ser Cys Glu Val Pro
    290                 295                 300

Ala Cys Thr His Ser Ser Asp Phe Gly Gly Val Ala Ile Ile Lys Tyr
305                 310                 315                 320

Thr Ala Ser Lys Lys Gly Lys Cys Ala Val His Ser Met Thr Asn Ala
                325                 330                 335

Val Thr Ile Arg Glu Ala Asp Val Glu Val Glu Gly Asn Ser Gln Leu
            340                 345                 350

```
Gln Ile Ser Phe Ser Thr Ala Leu Ala Ser Ala Glu Phe Arg Val Gln
            355                 360                 365

Val Cys Ser Thr Gln Val His Cys Ala Ala Cys His Pro Pro Lys
370                 375                 380

Asp His Ile Val Asn Tyr Pro Ala Ser His Thr Thr Leu Gly Val Gln
385                 390                 395                 400

Asp Ile Ser Thr Thr Ala Met Ser Trp Val Gln Lys Ile Thr Gly Gly
            405                 410                 415

Val Gly Leu Ile Val Ala Val Ala Ala Leu Ile Leu Ile Val Val Leu
            420                 425                 430

Cys Val Ser Phe Ser Arg His
            435

<210> SEQ ID NO 8
<211> LENGTH: 439
<212> TYPE: PRT
<213> ORGANISM: Artificial Sequence
<220> FEATURE:
<223> OTHER INFORMATION: Synthetic CHIKV E1 (OPY-1 strain)

<400> SEQUENCE: 8

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Val Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270
```

```
Val Gly Asn Met Pro Ile Ser Ile Asp Ile Pro Glu Ala Ala Phe Thr
                275                 280                 285

Arg Val Val Asp Ala Pro Ser Leu Thr Asp Met Ser Cys Glu Val Pro
290                 295                 300

Ala Cys Thr His Ser Ser Asp Phe Gly Gly Val Ala Ile Ile Lys Tyr
305                 310                 315                 320

Ala Ala Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
                340                 345                 350

Gln Ile Ser Phe Ser Thr Ala Leu Ala Ser Ala Glu Phe Arg Val Gln
                355                 360                 365

Val Cys Ser Thr Gln Val His Cys Ala Ala Glu Cys His Pro Pro Lys
                370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
                420                 425                 430

Cys Val Ser Phe Ser Arg His
                435

<210> SEQ ID NO 9
<211> LENGTH: 483
<212> TYPE: PRT
<213> ORGANISM: Artificial Sequence
<220> FEATURE:
<223> OTHER INFORMATION: Synthetic CHIKV E3-insert-E2 (37997 strain)

<400> SEQUENCE: 9

Ser Leu Ala Leu Pro Val Leu Cys Leu Leu Ala Asn Thr Thr Phe Pro
1               5                   10                  15

Cys Ser Gln Pro Pro Cys Thr Pro Cys Cys Tyr Glu Lys Glu Pro Glu
                20                  25                  30

Ser Thr Leu Arg Met Leu Glu Asp Asn Val Met Arg Pro Gly Tyr Tyr
                35                  40                  45

Gln Leu Leu Lys Ala Ser Leu Thr Cys Ser Pro His Ser Thr Lys Asp
50                  55                  60

Asn Phe Asn Val Tyr Lys Ala Thr Arg Pro Tyr Leu Ala His Cys Pro
65                  70                  75                  80

Asp Cys Gly Glu Gly His Ser Cys His Ser Pro Ile Ala Leu Glu Arg
                85                  90                  95

Ile Arg Asn Glu Ala Thr Asp Gly Thr Leu Lys Ile Gln Val Ser Leu
                100                 105                 110

Gln Ile Gly Ile Lys Thr Asp Asp Ser His Asp Trp Thr Lys Leu Arg
                115                 120                 125

Tyr Met Asp Ser His Thr Pro Ala Asp Ala Glu Arg Ala Gly Leu Leu
130                 135                 140

Val Arg Thr Ser Ala Pro Cys Thr Ile Thr Gly Thr Met Gly His Phe
145                 150                 155                 160

Ile Leu Ala Arg Cys Pro Lys Gly Glu Thr Leu Thr Val Gly Phe Thr
                165                 170                 175

Asp Ser Arg Lys Ile Ser His Thr Cys Thr His Pro Phe His His Glu
                180                 185                 190
```

-continued

```
Pro Pro Val Ile Gly Arg Glu Arg Phe His Ser Arg Pro Gln His Gly
            195                 200                 205
Lys Glu Leu Pro Cys Ser Thr Tyr Val Gln Ser Thr Ala Ala Thr Ala
210                 215                 220
Glu Glu Ile Glu Val His Met Pro Pro Asp Thr Pro Asp Arg Thr Leu
225                 230                 235                 240
Met Thr Gln Gln Ser Gly Asn Val Lys Ile Thr Val Asn Gly Gln Thr
            245                 250                 255
Val Arg Tyr Lys Cys Asn Cys Gly Gly Ser Asn Glu Gly Leu Thr Thr
            260                 265                 270
Thr Asp Lys Val Ile Asn Asn Cys Lys Ile Asp Gln Cys His Ala Ala
            275                 280                 285
Val Thr Asn His Lys Asn Trp Gln Tyr Asn Ser Pro Leu Val Pro Arg
290                 295                 300
Asn Ala Glu Leu Gly Asp Arg Lys Gly Lys Ile His Ile Pro Phe Pro
305                 310                 315                 320
Leu Ala Asn Val Thr Cys Arg Val Pro Lys Ala Arg Asn Pro Thr Val
            325                 330                 335
Thr Tyr Gly Lys Asn Gln Val Thr Met Leu Leu Tyr Pro Asp His Pro
            340                 345                 350
Thr Leu Leu Ser Tyr Arg Asn Met Gly Gln Glu Pro Asn Tyr His Glu
            355                 360                 365
Glu Trp Val Thr His Lys Lys Glu Val Thr Leu Thr Val Pro Thr Glu
            370                 375                 380
Gly Leu Glu Val Thr Trp Gly Asn Asn Glu Pro Tyr Lys Tyr Trp Pro
385                 390                 395                 400
Gln Met Ser Thr Asn Gly Thr Ala His Gly His Pro His Glu Ile Ile
            405                 410                 415
Leu Tyr Tyr Tyr Glu Leu Tyr Pro Thr Met Thr Val Ile Val Ser
            420                 425                 430
Val Ala Ser Phe Val Leu Leu Ser Met Val Gly Thr Ala Val Gly Met
            435                 440                 445
Cys Val Cys Ala Arg Arg Arg Cys Ile Thr Pro Tyr Glu Leu Thr Pro
450                 455                 460
Gly Ala Thr Val Pro Phe Leu Leu Ser Leu Leu Cys Cys Val Arg Thr
465                 470                 475                 480
Thr Lys Ala

<210> SEQ ID NO 10
<211> LENGTH: 483
<212> TYPE: PRT
<213> ORGANISM: Artificial Sequence
<220> FEATURE:
<223> OTHER INFORMATION: Synthetic CHIKV E3-insert-E2 (OPY-1 strain)

<400> SEQUENCE: 10

Ser Leu Ala Ile Pro Val Met Cys Leu Leu Ala Asn Thr Thr Phe Pro
1               5                   10                  15
Cys Ser Gln Pro Pro Cys Thr Pro Cys Cys Tyr Glu Lys Glu Pro Glu
            20                  25                  30
Glu Thr Leu Arg Met Leu Glu Asp Asn Val Met Arg Pro Gly Tyr Tyr
            35                  40                  45
Gln Leu Leu Gln Ala Ser Leu Thr Cys Ser Pro His Ser Thr Lys Asp
            50                  55                  60
Asn Phe Asn Val Tyr Lys Ala Thr Arg Pro Tyr Leu Ala His Cys Pro
```

```
            65                  70                  75                  80
Asp Cys Gly Glu Gly His Ser Cys His Ser Pro Val Ala Leu Glu Arg
                85                  90                  95
Ile Arg Asn Glu Ala Thr Asp Gly Thr Leu Lys Ile Gln Val Ser Leu
               100                 105                 110
Gln Ile Gly Ile Lys Thr Asp Ser His Asp Trp Thr Lys Leu Arg
               115                 120                 125
Tyr Met Asp Asn His Met Pro Ala Asp Ala Glu Arg Ala Gly Leu Phe
               130                 135                 140
Val Arg Thr Ser Ala Pro Cys Thr Ile Thr Gly Thr Met Gly His Phe
145                150                 155                 160
Ile Leu Ala Arg Cys Pro Lys Gly Glu Thr Leu Thr Val Gly Phe Thr
               165                 170                 175
Asp Ser Arg Lys Ile Ser His Ser Cys Thr His Pro Phe His His Asp
               180                 185                 190
Pro Pro Val Ile Gly Arg Glu Lys Phe His Ser Arg Pro Gln His Gly
               195                 200                 205
Lys Glu Leu Pro Cys Ser Thr Tyr Val Gln Ser Thr Ala Ala Thr Thr
               210                 215                 220
Glu Glu Ile Glu Val His Met Pro Pro Asp Thr Pro Asp Arg Thr Leu
225                230                 235                 240
Met Ser Gln Gln Ser Gly Asn Val Lys Ile Thr Val Asn Gly Gln Thr
               245                 250                 255
Val Arg Tyr Lys Cys Asn Cys Gly Gly Ser Asn Glu Gly Leu Thr Thr
               260                 265                 270
Thr Asp Lys Val Ile Asn Asn Cys Lys Val Asp Gln Cys His Ala Ala
               275                 280                 285
Val Thr Asn His Lys Lys Trp Gln Tyr Asn Ser Pro Leu Val Pro Arg
               290                 295                 300
Asn Ala Glu Leu Gly Asp Arg Lys Gly Lys Ile His Ile Pro Phe Pro
305                310                 315                 320
Leu Ala Asn Val Thr Cys Arg Val Pro Lys Ala Arg Asn Pro Thr Val
               325                 330                 335
Thr Tyr Gly Lys Asn Gln Val Ile Met Leu Leu Tyr Pro Asp His Pro
               340                 345                 350
Thr Leu Leu Ser Tyr Arg Asn Met Gly Glu Glu Pro Asn Tyr Gln Glu
               355                 360                 365
Glu Trp Val Met His Lys Lys Glu Val Val Leu Thr Val Pro Thr Glu
               370                 375                 380
Gly Leu Glu Val Thr Trp Gly Asn Asn Glu Pro Tyr Lys Tyr Trp Pro
385                390                 395                 400
Gln Leu Ser Thr Asn Gly Thr Ala His Gly His Pro His Glu Ile Ile
               405                 410                 415
Leu Tyr Tyr Tyr Glu Leu Tyr Pro Thr Met Thr Val Val Val Ser
               420                 425                 430
Val Ala Thr Phe Ile Leu Leu Ser Met Val Gly Met Ala Ala Gly Met
               435                 440                 445
Cys Met Cys Ala Arg Arg Arg Cys Ile Thr Pro Tyr Glu Leu Thr Pro
               450                 455                 460
Gly Ala Thr Val Pro Phe Leu Leu Ser Leu Ile Cys Cys Ile Arg Thr
465                470                 475                 480
Ala Lys Ala
```

<210> SEQ ID NO 11
<211> LENGTH: 3747
<212> TYPE: DNA
<213> ORGANISM: Artificial Sequence
<220> FEATURE:
<223> OTHER INFORMATION: Synthetic CHIKV sequence

<400> SEQUENCE: 11

```
atggagttca tcccgacgca aactttctat aacagaaggt accaaccccg accctgggcc     60
ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg aggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
cactccggag gcggatccag tactaaggac aattttaatg tctataaagc cacaagacca   1020
tatctagctc attgtcctga ctgcggagaa gggcattcgt gccacagccc tatcgcattg   1080
gagcgcatca gaaatgaagc aacggacgga acgctgaaaa tccaggtctc tttgcagatc   1140
gggataaaga cagatgacag ccacgattgg accaagctgc gctatatgga tagccatacg   1200
cccgcggacg cggagcgagc cggattgctt gtaaggactt cagcaccgtg cacgatcacc   1260
gggaccatgg gacactttat tctcgcccga tgcccgaaag gagagacgct gacagtggga   1320
tttacggaca gcagaaagat cagccacaca tgcacacacc cgttccatca tgaaccacct   1380
gtgataggta gggagaggtt ccactctcga ccacaacatg gtaaagagtt accttgcagc   1440
acgtacgtgc agagcaccgc tgccactgct gaggagatag aggtgcatat gcccccagat   1500
actcctgacc gcacgctgat gacgcagcag tctggcaacg tgaagatcac agttaatggg   1560
cagacggtgc ggtacaagtg caactgcggt ggctcaaacg agggactgac aaccacagac   1620
aaagtgatca ataactgcaa aattgatcag tgccatgctg cagtcactaa tcacaagaat   1680
tggcaataca actccccttt agtcccgcgc aacgctgaac tcggggaccg taaaggaaag   1740
atccacatcc cattcccatt ggcaaacgtg acttgcagag tgccaaaagc aagaaaccct   1800
acagtaactt acggaaaaaa ccaagtcacc atgctgctgt atcctgacca tccgacactc   1860
ttgtcttacc gtaacatggg acaggaacca aattaccacg aggagtgggt gacacacaag   1920
aaggaggtta ccttgaccgt gcctactgag ggtctggagg tcacttgggg caacaacgaa   1980
ccatacaagt actggccgca gatgtctacg aacggtactg ctcatggtca cccacatgag   2040
ataatcttgt actattatga gctgtacccc actatgactg tagtcattgt gtcggtggcc   2100
```

```
tcgttcgtgc ttctgtcgat ggtgggcaca gcagtgggaa tgtgtgtgtg cgcacggcgc    2160
agatgcatta caccatatga attaacacca ggagccactg ttcccttcct gctcagcctg    2220
ctatgctgcg tcagaacgac caaggcggcc acatattacg aggctgcggc atatctatgg    2280
aacgaacagc agcccctgtt ctggttgcag gctcttatcc cgctggccgc cttgatcgtc    2340
ctgtgcaact gtctgaaact cttgccatgc tgctgtaaga ccctggcttt tttagccgta    2400
atgagcatcg gtgcccacac tgtgagcgcg tacgaacacg taacagtgat cccgaacacg    2460
gtgggagtac cgtataagac tcttgtcaac agaccgggtt acagcccat ggtgttggag    2520 atggagctac aatcagtcac cttggaacca acactgtcac ttgactacat cacgtgcgag    2580
tacaaaactg tcatcccctc cccgtacgtg aagtgctgtg gtacagcaga gtgcaaggac    2640
aagagcctac cagactacag ctgcaaggtc tttactggag tctacccatt tatgtggggc    2700
ggcgcctact gcttttgcga cgccgaaaat acgcaattga gcgaggcaca tgtagagaaa    2760
tctgaatctt gcaaaacaga gtttgcatcg gcctacagag cccacaccgc atcggcgtcg    2820
gcgaagctcc gcgtcctta ccaaggaaac aacattaccg tagctgccta cgctaacggt    2880
gaccatgccg tcacagtaaa ggacgccaag tttgtcgtgg gcccaatgtc ctccgcctgg    2940 acacctttg acaacaaaat cgtggtgtac aaaggcgacg tctacaacat ggactaccca    3000 cctttggcg caggaagacc aggacaattt ggtgacattc aaagtcgtac accgaaagt    3060 aaagacgttt atgccaacac tcagttggta ctacagaggc cagcagcagg cacggtacat    3120
gtaccatact ctcaggcacc atctggcttc aagtattggc tgaaggaacg aggagcatcg    3180
ctacagcaca cggcaccgtt cggttgccag attgcgacaa cccggtaag agctgtaaat    3240 tgcgctgtgg ggaacatacc aatttccatc gacataccgg atgcggcctt tactagggtt    3300
gtcgatgcac cctctgtaac ggacatgtca tgcgaagtac cagcctgcac tcactcctcc    3360
gactttgggg gcgtcgccat catcaaatac acagctagca gaaaggtaa atgtgcagta    3420 cattcgatga ccaacgccgt taccattcga gaagccgacg tagaagtaga ggggaactcc    3480
cagctgcaaa tatccttctc aacagcccctg gcaagcgccg agtttcgcgt gcaagtgtgc    3540
tccacacaag tacactgcgc agccgcatgc caccctccaa aggaccacat agtcaattac    3600
ccagcatcac acaccacccct tggggtccag gatatatcca caacggcaat gtcttgggtg    3660
cagaagatta cgggaggagt aggattaatt gttgctgttg ctgccttaat tttaattgtg    3720
gtgctatgcg tgtcgtttag caggcac                                        3747
```

<210> SEQ ID NO 12
<211> LENGTH: 1255
<212> TYPE: PRT
<213> ORGANISM: Venezuelan equine encephalitis virus
<220> FEATURE:
<221> NAME/KEY: misc_feature
<222> LOCATION: (758)..(813)
<223> OTHER INFORMATION: 6K

<400> SEQUENCE: 12

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Ala

-continued

```
                50                  55                  60
Lys Pro Lys Lys Glu Ala Ser Gln Lys Gln Lys Gly Gly Gln Gly
 65                  70                  75                  80
Lys Lys Lys Lys Asn Gln Gly Lys Lys Ala Lys Thr Gly Pro Pro
                    85                  90                  95
Asn Pro Lys Ala Gln Asn Gly Asn Lys Lys Thr Asn Lys Lys Pro
                100                 105                 110
Gly Lys Arg Gln Arg Met Val Met Lys Leu Glu Ser Asp Lys Thr Phe
                115                 120                 125
Pro Ile Met Leu Glu Gly Lys Ile Asn Gly Tyr Ala Cys Val Val Gly
                130                 135                 140
Gly Lys Leu Phe Arg Pro Met His Val Glu Gly Lys Ile Asp Asn Asp
145                 150                 155                 160
Val Leu Ala Ala Leu Lys Thr Lys Lys Ala Ser Lys Tyr Asp Leu Glu
                165                 170                 175
Tyr Ala Asp Val Pro Gln Asn Met Arg Ala Asp Thr Phe Lys Tyr Thr
                180                 185                 190
His Glu Lys Pro Gln Gly Tyr Tyr Ser Trp His His Gly Ala Val Gln
                195                 200                 205
Tyr Glu Asn Gly Arg Phe Thr Val Pro Lys Gly Val Gly Ala Lys Gly
                210                 215                 220
Asp Ser Gly Arg Pro Ile Leu Asp Asn Gln Gly Arg Val Val Ala Ile
225                 230                 235                 240
Val Leu Gly Gly Val Asn Glu Gly Ser Arg Thr Ala Leu Ser Val Val
                    245                 250                 255
Met Trp Asn Glu Lys Gly Val Thr Val Lys Tyr Thr Pro Glu Asn Cys
                    260                 265                 270
Glu Gln Trp Ser Leu Val Thr Thr Met Cys Leu Leu Ala Asn Val Thr
                    275                 280                 285
Phe Pro Cys Ala Gln Pro Pro Ile Cys Tyr Asp Arg Lys Pro Ala Glu
                290                 295                 300
Thr Leu Ala Met Leu Ser Val Asn Val Asp Asn Pro Gly Tyr Asp Glu
305                 310                 315                 320
Leu Leu Glu Ala Ala Val Lys Cys Pro Gly Arg Lys Arg Arg Ser Thr
                    325                 330                 335
Glu Glu Leu Phe Asn Glu Tyr Lys Leu Thr Arg Pro Tyr Met Ala Arg
                    340                 345                 350
Cys Ile Arg Cys Ala Val Gly Ser Cys His Ser Pro Ile Ala Ile Glu
                    355                 360                 365
Ala Val Lys Ser Asp Gly His Asp Gly Tyr Val Arg Leu Gln Thr Ser
                    370                 375                 380
Ser Gln Tyr Gly Leu Asp Ser Ser Gly Asn Leu Lys Gly Arg Thr Met
385                 390                 395                 400
Arg Tyr Asp Met His Gly Thr Ile Lys Glu Ile Pro Leu His Gln Val
                    405                 410                 415
Ser Leu Tyr Thr Ser Arg Pro Cys His Ile Val Asp Gly His Gly Tyr
                    420                 425                 430
Phe Leu Leu Ala Arg Cys Pro Ala Gly Asp Ser Ile Thr Met Glu Phe
                    435                 440                 445
Lys Lys Asp Ser Val Arg His Ser Cys Ser Val Pro Tyr Glu Val Lys
                    450                 455                 460
Phe Asn Pro Val Gly Arg Glu Leu Tyr Thr His Pro Pro Glu His Gly
465                 470                 475                 480
```

```
Val Glu Gln Ala Cys Gln Val Tyr Ala His Asp Ala Gln Asn Arg Gly
                485                 490                 495
Ala Tyr Val Glu Met His Leu Pro Gly Ser Glu Val Asp Ser Ser Leu
            500                 505                 510
Val Ser Leu Ser Gly Ser Ser Val Thr Val Pro Pro Asp Gly Thr
        515                 520                 525
Ser Ala Leu Val Glu Cys Glu Cys Gly Gly Thr Lys Ile Ser Glu Thr
    530                 535                 540
Ile Asn Lys Thr Lys Gln Phe Ser Gln Cys Thr Lys Lys Glu Gln Cys
545                 550                 555                 560
Arg Ala Tyr Arg Leu Gln Asn Asp Lys Trp Val Tyr Asn Ser Asp Lys
                565                 570                 575
Leu Pro Lys Ala Ala Gly Ala Thr Leu Lys Gly Lys Leu His Val Pro
            580                 585                 590
Phe Leu Leu Ala Asp Gly Lys Cys Thr Val Pro Leu Ala Pro Glu Pro
        595                 600                 605
Met Ile Thr Phe Gly Phe Arg Ser Val Ser Leu Lys Leu His Pro Lys
    610                 615                 620
Asn Pro Thr Tyr Leu Ile Thr Arg Gln Leu Ala Asp Glu Pro His Tyr
625                 630                 635                 640
Thr His Glu Leu Ile Ser Glu Pro Ala Val Arg Asn Phe Thr Val Thr
                645                 650                 655
Glu Lys Gly Trp Glu Phe Val Trp Gly Asn His Pro Pro Lys Arg Phe
            660                 665                 670
Trp Ala Gln Glu Thr Ala Pro Gly Asn Pro His Gly Leu Pro His Glu
        675                 680                 685
Val Ile Thr His Tyr Tyr His Arg Tyr Pro Met Ser Thr Ile Leu Gly
    690                 695                 700
Leu Ser Ile Cys Ala Ala Ile Ala Thr Val Ser Val Ala Ala Ser Thr
705                 710                 715                 720
Trp Leu Phe Cys Arg Ser Arg Val Ala Cys Leu Thr Pro Tyr Arg Leu
                725                 730                 735
Thr Pro Asn Ala Arg Ile Pro Phe Cys Leu Ala Val Leu Cys Cys Ala
            740                 745                 750
Arg Thr Ala Arg Ala Glu Thr Thr Trp Glu Ser Leu Asp His Leu Trp
        755                 760                 765
Asn Asn Asn Gln Gln Met Phe Trp Ile Gln Leu Leu Ile Pro Leu Ala
    770                 775                 780
Ala Leu Ile Val Val Thr Arg Leu Leu Arg Cys Val Cys Cys Val Val
785                 790                 795                 800
Pro Phe Leu Val Met Ala Gly Ala Ala Gly Ala Gly Ala Tyr Glu His
                805                 810                 815
Ala Thr Thr Met Pro Ser Gln Ala Gly Ile Ser Tyr Asn Thr Ile Val
            820                 825                 830
Asn Arg Ala Gly Tyr Ala Pro Leu Pro Ile Ser Ile Thr Pro Thr Lys
        835                 840                 845
Ile Lys Leu Ile Pro Thr Val Asn Leu Glu Tyr Val Thr Cys His Tyr
    850                 855                 860
Lys Thr Gly Met Asp Ser Pro Ala Ile Lys Cys Cys Gly Ser Gln Glu
865                 870                 875                 880
Cys Thr Pro Thr Tyr Arg Pro Asp Glu Gln Cys Lys Val Phe Thr Gly
                885                 890                 895
```

-continued

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
        915                 920                 925

Ala Asp His Ala Glu Ala Tyr Lys Ala His Thr Ala Ser Val Gln Ala
    930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
            980                 985                 990

Tyr Ala Gly Glu Ile Tyr Asn Tyr Asp Phe Pro Glu Tyr Gly Ala Gly
        995                 1000                1005

Gln Pro Gly Ala Phe Gly Asp Ile Gln Ser Arg Thr Val Ser Ser
    1010                1015                1020

Ser Asp Leu Tyr Ala Asn Thr Asn Leu Val Leu Gln Arg Pro Lys
    1025                1030                1035

Ala Gly Ala Ile His Val Pro Tyr Thr Gln Ala Pro Ser Gly Phe
    1040                1045                1050

Glu Gln Trp Lys Lys Asp Lys Ala Pro Ser Leu Lys Phe Thr Ala
    1055                1060                1065

Pro Phe Gly Cys Glu Ile Tyr Thr Asn Pro Ile Arg Ala Glu Asn
    1070                1075                1080

Cys Ala Val Gly Ser Ile Pro Leu Ala Phe Asp Ile Pro Asp Ala
    1085                1090                1095

Leu Phe Thr Arg Val Ser Glu Thr Pro Thr Leu Ser Ala Ala Glu
    1100                1105                1110

Cys Thr Leu Asn Glu Cys Val Tyr Ser Ser Asp Phe Gly Gly Ile
    1115                1120                1125

Ala Thr Val Lys Tyr Ser Ala Ser Lys Ser Gly Lys Cys Ala Val
    1130                1135                1140

His Val Pro Ser Gly Thr Ala Thr Leu Lys Glu Ala Ala Val Glu
    1145                1150                1155

Leu Thr Glu Gln Gly Ser Ala Thr Ile His Phe Ser Thr Ala Asn
    1160                1165                1170

Ile His Pro Glu Phe Arg Leu Gln Ile Cys Thr Ser Tyr Val Thr
    1175                1180                1185

Cys Lys Gly Asp Cys His Pro Pro Lys Asp His Ile Val Thr His
    1190                1195                1200

Pro Gln Tyr His Ala Gln Thr Phe Thr Ala Ala Val Ser Lys Thr
    1205                1210                1215

Ala Trp Thr Trp Leu Thr Ser Leu Leu Gly Gly Ser Ala Val Ile
    1220                1225                1230

Ile Ile Ile Gly Leu Val Leu Ala Thr Ile Val Ala Met Tyr Val
    1235                1240                1245

Leu Thr Asn Gln Lys His Asn
    1250                1255

<210> SEQ ID NO 13
<211> LENGTH: 56
<212> TYPE: PRT
<213> ORGANISM: Artificial Sequence
<220> FEATURE:
<223> OTHER INFORMATION: Synthetic VEEV TC-83 strain 6K sequence

<400> SEQUENCE: 13

Glu Thr Thr Trp Glu Ser Leu Asp His Leu Trp Asn Asn Asn Gln Gln
1               5                   10                  15

Met Phe Trp Ile Gln Leu Leu Ile Pro Leu Ala Ala Leu Ile Val Val
            20                  25                  30

Thr Arg Leu Leu Arg Cys Val Cys Cys Val Val Pro Phe Leu Val Met
        35                  40                  45

Ala Gly Ala Ala Gly Ala Gly Ala
    50                  55

<210> SEQ ID NO 14
<211> LENGTH: 275
<212> TYPE: PRT
<213> ORGANISM: Artificial Sequence
<220> FEATURE:
<223> OTHER INFORMATION: Synthetic VEEV Capsid

<400> SEQUENCE: 14

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Asn Gly Asn Lys Lys Thr Asn Lys Lys Pro
            100                 105                 110

Gly Lys Arg Gln Arg Met Val Met Lys Leu Glu Ser Asp Lys Thr Phe
            115                 120                 125

Pro Ile Met Leu Glu Gly Lys Ile Asn Gly Tyr Ala Cys Val Val Gly
        130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
    275

```
<210> SEQ ID NO 15
<211> LENGTH: 442
<212> TYPE: PRT
<213> ORGANISM: Artificial Sequence
<220> FEATURE:
<223> OTHER INFORMATION: Synthetic VEEV E1

<400> SEQUENCE: 15

Tyr Glu His Ala Thr Thr Met Pro Ser Gln Ala Gly Ile Ser Tyr Asn
1               5                   10                  15

Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
        35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
    130                 135                 140

Thr Val Tyr Val Asn Gly Glu Thr Pro Val Asn Phe Asn Gly Val Lys
145                 150                 155                 160

Ile Thr Ala Gly Pro Leu Ser Thr Ala Trp Thr Pro Phe Asp Arg Lys
                165                 170                 175

Ile Val Gln Tyr Ala Gly Glu Ile Tyr Asn Tyr Asp Phe Pro Glu Tyr
            180                 185                 190

Gly Ala Gly Gln Pro Gly Ala Phe Gly Asp Ile Gln Ser Arg Thr Val
        195                 200                 205

Ser Ser Ser Asp Leu Tyr Ala Asn Thr Asn Leu Val Leu Gln Arg Pro
    210                 215                 220

Lys Ala Gly Ala Ile His Val Pro Tyr Thr Gln Ala Pro Ser Gly Phe
225                 230                 235                 240

Glu Gln Trp Lys Lys Asp Lys Ala Pro Ser Leu Lys Phe Thr Ala Pro
                245                 250                 255

Phe Gly Cys Glu Ile Tyr Thr Asn Pro Ile Arg Ala Glu Asn Cys Ala
            260                 265                 270

Val Gly Ser Ile Pro Leu Ala Phe Asp Ile Pro Asp Ala Leu Phe Thr
        275                 280                 285

Arg Val Ser Glu Thr Pro Thr Leu Ser Ala Ala Glu Cys Thr Leu Asn
    290                 295                 300

Glu Cys Val Tyr Ser Ser Asp Phe Gly Gly Ile Ala Thr Val Lys Tyr
305                 310                 315                 320

Ser Ala Ser Lys Ser Gly Lys Cys Ala Val His Val Pro Ser Gly Thr
                325                 330                 335

Ala Thr Leu Lys Glu Ala Ala Val Glu Leu Thr Glu Gln Gly Ser Ala
            340                 345                 350

Thr Ile His Phe Ser Thr Ala Asn Ile His Pro Glu Phe Arg Leu Gln
        355                 360                 365
```

Ile Cys Thr Ser Tyr Val Thr Cys Lys Gly Asp Cys His Pro Pro Lys
370                 375                 380

Asp His Ile Val Thr His Pro Gln Tyr His Ala Gln Thr Phe Thr Ala
385                 390                 395                 400

Ala Val Ser Lys Thr Ala Trp Thr Trp Leu Thr Ser Leu Leu Gly Gly
            405                 410                 415

Ser Ala Val Ile Ile Ile Ile Gly Leu Val Leu Ala Thr Ile Val Ala
            420                 425                 430

Met Tyr Val Leu Thr Asn Gln Lys His Asn
            435                 440

<210> SEQ ID NO 16
<211> LENGTH: 1260
<212> TYPE: PRT
<213> ORGANISM: Artificial Sequence
<220> FEATURE:
<223> OTHER INFORMATION: Synthetic VEEV E3-insert-E2

<400> SEQUENCE: 16

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Asn Gly Asn Lys Lys Thr Asn Lys Lys Pro
                100                 105                 110

Gly Lys Arg Gln Arg Met Val Met Lys Leu Glu Ser Asp Lys Thr Phe
            115                 120                 125

Pro Ile Met Leu Glu Gly Lys Ile Asn Gly Tyr Ala Cys Val Val Gly
130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
            165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
            195                 200                 205

Tyr Glu Asn Gly Arg Phe Thr Val Pro Lys Gly Val Gly Ala Lys Gly
            210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
            245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
            275                 280                 285

-continued

```
Phe Pro Cys Ala Gln Pro Pro Ile Cys Tyr Asp Arg Lys Pro Ala Glu
    290                 295                 300
Thr Leu Ala Met Leu Ser Val Asn Val Asp Asn Pro Gly Tyr Asp Glu
305                 310                 315                 320
Leu Leu Glu Ala Ala Val Lys Cys Pro Gly Ser Gly Gly Ser Ser
                325                 330                 335
Thr Glu Glu Leu Phe Asn Glu Tyr Lys Leu Thr Arg Pro Tyr Met Ala
                340                 345                 350
Arg Cys Ile Arg Cys Ala Val Gly Ser Cys His Ser Pro Ile Ala Ile
            355                 360                 365
Glu Ala Val Lys Ser Asp Gly His Asp Gly Tyr Val Arg Leu Gln Thr
370                 375                 380
Ser Ser Gln Tyr Gly Leu Asp Ser Ser Gly Asn Leu Lys Gly Arg Thr
385                 390                 395                 400
Met Arg Tyr Asp Met His Gly Thr Ile Lys Glu Ile Pro Leu His Gln
                405                 410                 415
Val Ser Leu Tyr Thr Ser Arg Pro Cys His Ile Val Asp Gly His Gly
            420                 425                 430
Tyr Phe Leu Leu Ala Arg Cys Pro Ala Gly Asp Ser Ile Thr Met Glu
        435                 440                 445
Phe Lys Lys Asp Ser Val Arg His Ser Cys Ser Val Pro Tyr Glu Val
    450                 455                 460
Lys Phe Asn Pro Val Gly Arg Glu Leu Tyr Thr His Pro Pro Glu His
465                 470                 475                 480
Gly Val Glu Gln Ala Cys Gln Val Tyr Ala His Asp Ala Gln Asn Arg
                485                 490                 495
Gly Ala Tyr Val Glu Met His Leu Pro Gly Ser Glu Val Asp Ser Ser
                500                 505                 510
Leu Val Ser Leu Ser Gly Ser Ser Gly Ser Ser Val Thr Val Thr
            515                 520                 525
Pro Pro Asp Gly Thr Ser Ala Leu Val Glu Cys Glu Cys Gly Gly Thr
530                 535                 540
Lys Ile Ser Glu Thr Ile Asn Lys Thr Lys Gln Phe Ser Gln Cys Thr
545                 550                 555                 560
Lys Lys Glu Gln Cys Arg Ala Tyr Arg Leu Gln Asn Asp Lys Trp Val
                565                 570                 575
Tyr Asn Ser Asp Lys Leu Pro Lys Ala Ala Gly Ala Thr Leu Lys Gly
                580                 585                 590
Lys Leu His Val Pro Phe Leu Leu Ala Asp Gly Lys Cys Thr Val Pro
            595                 600                 605
Leu Ala Pro Glu Pro Met Ile Thr Phe Gly Phe Arg Ser Val Ser Leu
610                 615                 620
Lys Leu His Pro Lys Asn Pro Thr Tyr Leu Ile Thr Arg Gln Leu Ala
625                 630                 635                 640
Asp Glu Pro His Tyr Thr His Glu Leu Ile Ser Glu Pro Ala Val Arg
                645                 650                 655
Asn Phe Thr Val Thr Glu Lys Gly Trp Glu Phe Val Trp Gly Asn His
            660                 665                 670
Pro Pro Lys Arg Phe Trp Ala Gln Glu Thr Ala Pro Gly Asn Pro His
        675                 680                 685
Gly Leu Pro His Glu Val Ile Thr His Tyr Tyr His Arg Tyr Pro Met
    690                 695                 700
Ser Thr Ile Leu Gly Leu Ser Ile Cys Ala Ala Ile Ala Thr Val Ser
```

```
705                 710                 715                 720
Val Ala Ala Ser Thr Trp Leu Phe Cys Arg Ser Arg Val Ala Cys Leu
                725                 730                 735
Thr Pro Tyr Arg Leu Thr Pro Asn Ala Arg Ile Pro Phe Cys Leu Ala
                740                 745                 750
Val Leu Cys Cys Ala Arg Thr Arg Ala Glu Thr Thr Trp Glu Ser
                755                 760                 765
Leu Asp His Leu Trp Asn Asn Asn Gln Gln Met Phe Trp Ile Gln Leu
                770                 775                 780
Leu Ile Pro Leu Ala Ala Leu Ile Val Val Thr Arg Leu Leu Arg Cys
785                 790                 795                 800
Val Cys Cys Val Val Pro Phe Leu Val Met Ala Gly Ala Ala Gly Ala
                805                 810                 815
Gly Ala Tyr Glu His Ala Thr Thr Met Pro Ser Gln Ala Gly Ile Ser
                820                 825                 830
Tyr Asn Thr Ile Val Asn Arg Ala Gly Tyr Ala Pro Leu Pro Ile Ser
                835                 840                 845
Ile Thr Pro Thr Lys Ile Lys Leu Ile Pro Thr Val Asn Leu Glu Tyr
                850                 855                 860
Val Thr Cys His Tyr Lys Thr Gly Met Asp Ser Pro Ala Ile Lys Cys
865                 870                 875                 880
Cys Gly Ser Gln Glu Cys Thr Pro Thr Tyr Arg Pro Asp Glu Gln Cys
                885                 890                 895
Lys Val Phe Thr Gly Val Tyr Pro Phe Met Trp Gly Gly Ala Tyr Cys
                900                 905                 910
Phe Cys Asp Thr Glu Asn Thr Gln Val Ser Lys Ala Tyr Val Met Lys
                915                 920                 925
Ser Asp Asp Cys Leu Ala Asp His Ala Glu Ala Tyr Lys Ala His Thr
                930                 935                 940
Ala Ser Val Gln Ala Phe Leu Asn Ile Thr Val Gly Glu His Ser Ile
945                 950                 955                 960
Val Thr Thr Val Tyr Val Asn Gly Glu Thr Pro Val Asn Phe Asn Gly
                965                 970                 975
Val Lys Ile Thr Ala Gly Pro Leu Ser Thr Ala Trp Thr Pro Phe Asp
                980                 985                 990
Arg Lys Ile Val Gln Tyr Ala Gly Glu Ile Tyr Asn Tyr Asp Phe Pro
                995                 1000                1005
Glu Tyr Gly Ala Gly Gln Pro Gly Ala Phe Gly Asp Ile Gln Ser
                1010                1015                1020
Arg Thr Val Ser Ser Ser Asp Leu Tyr Ala Asn Thr Asn Leu Val
                1025                1030                1035
Leu Gln Arg Pro Lys Ala Gly Ala Ile His Val Pro Tyr Thr Gln
                1040                1045                1050
Ala Pro Ser Gly Phe Glu Gln Trp Lys Lys Asp Lys Ala Pro Ser
                1055                1060                1065
Leu Lys Phe Thr Ala Pro Phe Gly Cys Glu Ile Tyr Thr Asn Pro
                1070                1075                1080
Ile Arg Ala Glu Asn Cys Ala Val Gly Ser Ile Pro Leu Ala Phe
                1085                1090                1095
Asp Ile Pro Asp Ala Leu Phe Thr Arg Val Ser Glu Thr Pro Thr
                1100                1105                1110
Leu Ser Ala Ala Glu Cys Thr Leu Asn Glu Cys Val Tyr Ser Ser
                1115                1120                1125
```

```
Asp Phe Gly Gly Ile Ala Thr Val Lys Tyr Ser Ala Ser Lys Ser
    1130                1135                1140

Gly Lys Cys Ala Val His Val Pro Ser Gly Thr Ala Thr Leu Lys
    1145                1150                1155

Glu Ala Ala Val Glu Leu Thr Glu Gln Gly Ser Ala Thr Ile His
    1160                1165                1170

Phe Ser Thr Ala Asn Ile His Pro Glu Phe Arg Leu Gln Ile Cys
    1175                1180                1185

Thr Ser Tyr Val Thr Cys Lys Gly Asp Cys His Pro Pro Lys Asp
    1190                1195                1200

His Ile Val Thr His Pro Gln Tyr His Ala Gln Thr Phe Thr Ala
    1205                1210                1215

Ala Val Ser Lys Thr Ala Trp Thr Trp Leu Thr Ser Leu Leu Gly
    1220                1225                1230

Gly Ser Ala Val Ile Ile Ile Gly Leu Val Leu Ala Thr Ile
    1235                1240                1245

Val Ala Met Tyr Val Leu Thr Asn Gln Lys His Asn
    1250                1255                1260
```

```
<210> SEQ ID NO 17
<211> LENGTH: 3768
<212> TYPE: DNA
<213> ORGANISM: Artificial Sequence
<220> FEATURE:
<223> OTHER INFORMATION: Synthetic VEEV

<400> SEQUENCE: 17
```

| | | | | | |
|---|---|---|---|---|---|
| atgttcccgt | tccagccaat | gtatccgatg | cagccaatgc | cctatcgcaa | cccgttcgcg | 60 |
| gccccgcgca | ggccctggtt | ccccagaacc | gacccttttc | tggcgatgca | ggtgcaggaa | 120 |
| ttaacccgct | cgatggctaa | cctgacgttc | aagcaacgcc | gggacgcgcc | acctgagggg | 180 |
| ccatccgcta | taaaccgaa | gaaggaggcc | tcgcaaaaac | agaaaggggg | aggccaaggg | 240 |
| aagaagaaga | gaaccaagg | gaagaagaag | gctaagacag | ggccgcctaa | tccgaaggca | 300 |
| cagaatggaa | acaagaagaa | gaccaacaag | aaaccaggca | agacagcg | catggtcatg | 360 |
| aaattggaat | ctgacaagac | gttcccaatc | atgttggaag | ggaagataaa | cggctacgct | 420 |
| tgtgtggtcg | gagggaagtt | attcaggccg | atgcatgtgg | aaggcaagat | cgacaacgac | 480 |
| gttctggccg | cgcttaagac | gaagaaagca | tccaaatacg | atcttgagta | tgcagatgtg | 540 |
| ccacagaaca | tgcgggccga | tacattcaaa | tacacccatg | agaaacccca | aggctattac | 600 |
| agctggcatc | atggagcagt | ccaatatgaa | aatgggcgtt | tcacggtgcc | gaaaggagtt | 660 |
| ggggccaagg | gagacagcgg | acgaccatt | ctggataacc | agggacgggt | ggtcgctatt | 720 |
| gtgctgggag | gtgtgaatga | aggatctagg | acagccettt | cagtcgtcat | gtggaacgag | 780 |
| aagggagtta | ccgtgaagta | tactccagag | aactgcgagc | aatggtcact | agtgaccacc | 840 |
| atgtgtctgc | tcgccaatgt | gacgttccca | tgtgctcaac | caccaatttg | ctacgacaga | 900 |
| aaaccagcag | agactttggc | catgctcagc | gttaacgttg | acaacccggg | ctacgatgag | 960 |
| ctgctggaag | cagctgttaa | gtgccccggg | tccggaggtg | atcctccac | cgaggagctg | 1020 |
| tttaatgagt | ataagctaac | gcgcccttac | atggccagat | gcatcagatg | tgcagttggg | 1080 |
| agctgccata | gtccaatagc | aatcgaggca | gtaaagagcg | acgggacga | cggttatgtt | 1140 |
| agacttcaga | cttcctcgca | gtatggcctg | gattcctccg | gcaacttaaa | gggcaggacc | 1200 |
| atgcggtatg | acatgcacgg | gaccattaaa | gagataccac | tacatcaagt | gtcactctat | 1260 |

```
acatctcgcc cgtgtcacat tgtggatggg cacggttatt tcctgctagc caggtgcccg    1320 gcagggggact ccatcaccat ggaatttaag aaagattccg tcagacactc ctgctcggtg    1380
ccgtatgaag tgaaatttaa tcctgtaggc agagaactct atactcatcc cccagaacac    1440
ggagtagagc aagcgtgcca agtctacgca catgatgcac agaacagagg agcttatgtc    1500
gagatgcacc tcccgggctc agaagtggac agcagtttgg tttccttgag cggcagttca    1560
gtcaccgtga cacctcctga tgggactagc gccctggtgg aatgcgagtg tggcggcaca    1620
aagatctccg agaccatcaa caagacaaaa cagttcagcc agtgcacaaa gaaggagcag    1680
tgcagagcat atcggctgca gaacgataag tgggtgtata attctgacaa actgcccaaa    1740
gcagcgggag ccaccttaaa aggaaaactg catgtcccat tcttgctggc agacggcaaa    1800
tgcaccgtgc ctctagcacc agaacctatg ataaccttcg gtttcagatc agtgtcactg    1860
aaactgcacc ctaagaatcc cacatatcta atcacccgcc aacttgctga tgagcctcac    1920
tacacgcacg agctcatatc tgaaccagct gttaggaatt ttaccgtcac cgaaaaaggg    1980
tgggagtttg tatggggaaa ccacccgccg aaaaggtttt gggcacagga aacagcaccc    2040
ggaaatccac atgggctacc gcacgagtg ataactcatt attaccacag ataccctatg    2100
tccaccatcc tgggtttgtc aatttgtgcc gccattgcaa ccgtttccgt tgcagcgtct    2160
acctggctgt tttgcagatc aagagttgcg tgcctaactc cttaccggct aacacctaac    2220
gctaggatac cattttgtct ggctgtgctt tgctgcgccc gcactgcccg ggccgagacc    2280
acctgggagt ccttggatca cctatggaac aataaccaac agatgttctg gattcaattg    2340
ctgatccctc tggccgcctt gatcgtagtg actcgcctgc tcaggtgcgt gtgctgtgtc    2400
gtgccttttt tagtcatggc cggcgccgca ggcgccggcg cctacagcag cgcgaccacg    2460
atgccgagcc aagcgggaat ctcgtataac actatagtca acagagcagg ctacgcacca    2520
ctccctatca gcataacacc aacaaagatc aagctgatac ctacagtgaa cttggagtac    2580
gtcacctgcc actacaaaac aggaatggat tcaccagcca tcaaatgctg cggatctcag    2640
gaatgcactc caacttacag gcctgatgaa cagtgcaaag tcttcacagg ggtttacccg    2700
ttcatgtggg gtggtgcata ttgcttttgc gacactgaga cacccaagt cagcaaggcc    2760 tacgtaatga aatctgacga ctgccttgcg gatcatgctg aagcatataa agcgcacaca    2820
gcctcagtgc aggcgttcct caacatcaca gtgggagaac actctattgt gactaccgtg    2880
tatgtgaatg gagaaactcc tgtgaatttc aatggggtca aaataactgc aggtccgctt    2940
tccacagctt ggacaccctt tgatcgcaaa atcgtgcagt atgccgggga gatctataat    3000
tatgattttc ctgagtatgg ggcaggacaa ccaggagcat tggagatat acaatccaga    3060 acagtctcaa gctctgatct gtatgccaat accaacctag tgctgcagag acccaaagca    3120
ggagcgatcc acgtgccata cactcaggca ccttcgggtt ttgagcaatg gaagaaagat    3180
aaagctccat cattgaaatt taccgcccct ttcggatgcg aaatatatac aaaccccatt    3240
cgcgccgaaa actgtgctgt agggtcaatt ccattagcct ttgacattcc cgacgccttg    3300
ttcaccaggg tgtcagaaac accgacactt cagcgccg aatgcactct taacgagtgc    3360
gtgtattctt ccgactttgg tgggatcgcc acgtcaagt actcggccag caagtcaggc    3420
aagtgcgcag tccatgtgcc atcagggact gctaccctaa agaagcagc agtcgagcta    3480 accgagcaag ggtcggcgac tatccatttc tcgaccgcaa atatccaccc ggagttcagg    3540
ctccaaatat gcacatcata tgttacgtgc aaaggtgatt gtcacccccc gaaagaccat    3600
```

-continued

| | | | | | |
|---|---|---|---|---|---|
| attgtgacac | accctcagta | tcacgcccaa | acatttacag | ccgcggtgtc | aaaaaccgcg 3660 |
| tggacgtggt | taacatccct | gctgggagga | tcagccgtaa | ttattataat | tggcttggtg 3720 |
| ctggctacta | ttgtggccat | gtacgtgctg | accaaccaga | aacataat | 3768 |